US00PP18890P2

(12) United States Plant Patent
Bakhuijzen

(10) Patent No.: US PP18,890 P2
(45) Date of Patent: Jun. 3, 2008

(54) ***CORTADERIA* PLANT NAMED 'SILVER STAR '**

(50) Latin Name: *Cortaderia selloana*
Varietal Denomination: Silver Star

(75) Inventor: Arie Bakhuijzen, Boskoop (NL)

(73) Assignee: Gebroeders V.D. Salm B.V., Boskoop (NL)

( * ) Notice: Subject to any disclaimer, the term of this patent is extended or adjusted under 35 U.S.C. 154(b) by 0 days.

(21) Appl. No.: 11/599,021

(22) Filed: Nov. 14, 2006

(51) Int. Cl.
*A01H 5/00* (2006.01)

(52) U.S. Cl. ..... Plt./384
(58) Field of Classification Search ..... Plt./384
See application file for complete search history.

*Primary Examiner*—Annette H Para
(74) *Attorney, Agent, or Firm*—Jondle & Associates, P.C.

(57) ABSTRACT

A new variety of *Cortaderia* plant particularly distinguished by having a broad inverted triangle shape with arching leaves and greyed-green inflorescences, long green leaves with yellow-green stripes, moderate vigor and hardiness to at least USDA zone, is disclosed.

3 Drawing Sheets

Genus/species: *Cortaderia selloana.*

BACKGROUND OF THE INVENTION

The present invention comprises a new and distinct cultivar of pampas grass, botanically known as *Cortaderia selloana,* and hereinafter referred to by the cultivar name 'Silver Star'. The new cultivar originated as a whole-plant mutation from *Cortaderia selloana* 'Pumila' (unpatented). The new cultivar was found in the breeder's nursery in Boskoop, The Netherlands, in 2000.

The new cultivar was created in 2000 and has been asexually reproduced repeatedly by division in Boskoop, The Netherlands over a five-year period. 'Silver Star' has not been observed under all possible environmental conditions. The present invention has been found to retain its distinctive characteristics through successive asexual propagations.

Plant Breeder's Rights for this cultivar were applied for with the European Union on Jan. 24, 2006.

SUMMARY OF THE INVENTION

The following are the most outstanding and distinguishing characteristics of this new cultivar when grown under normal horticultural practices in Boskoop, The Netherlands:

1. A perennial with a broad inverted triangle shape with arching leaves and greyed-green inflorescences;
2. Long green leaves with yellow-green stripes;
3. Moderate vigor; and
4. A hardiness to at least USDA zone 7.

DESCRIPTION OF THE PHOTOGRAPHS

This new *Cortaderia* plant is illustrated by the accompanying photographs which show overall plant habit including inflorescence, and foliage of the plant; the colors shown are as true as can be reasonably obtained by conventional photographic procedures. The photographs are from a whole plant about two-years old and grown in a 19-cm pot outdoors in Boskoop, The Netherlands.

DETAILED DESCRIPTION OF THE NEW PLANT

Figure 1:
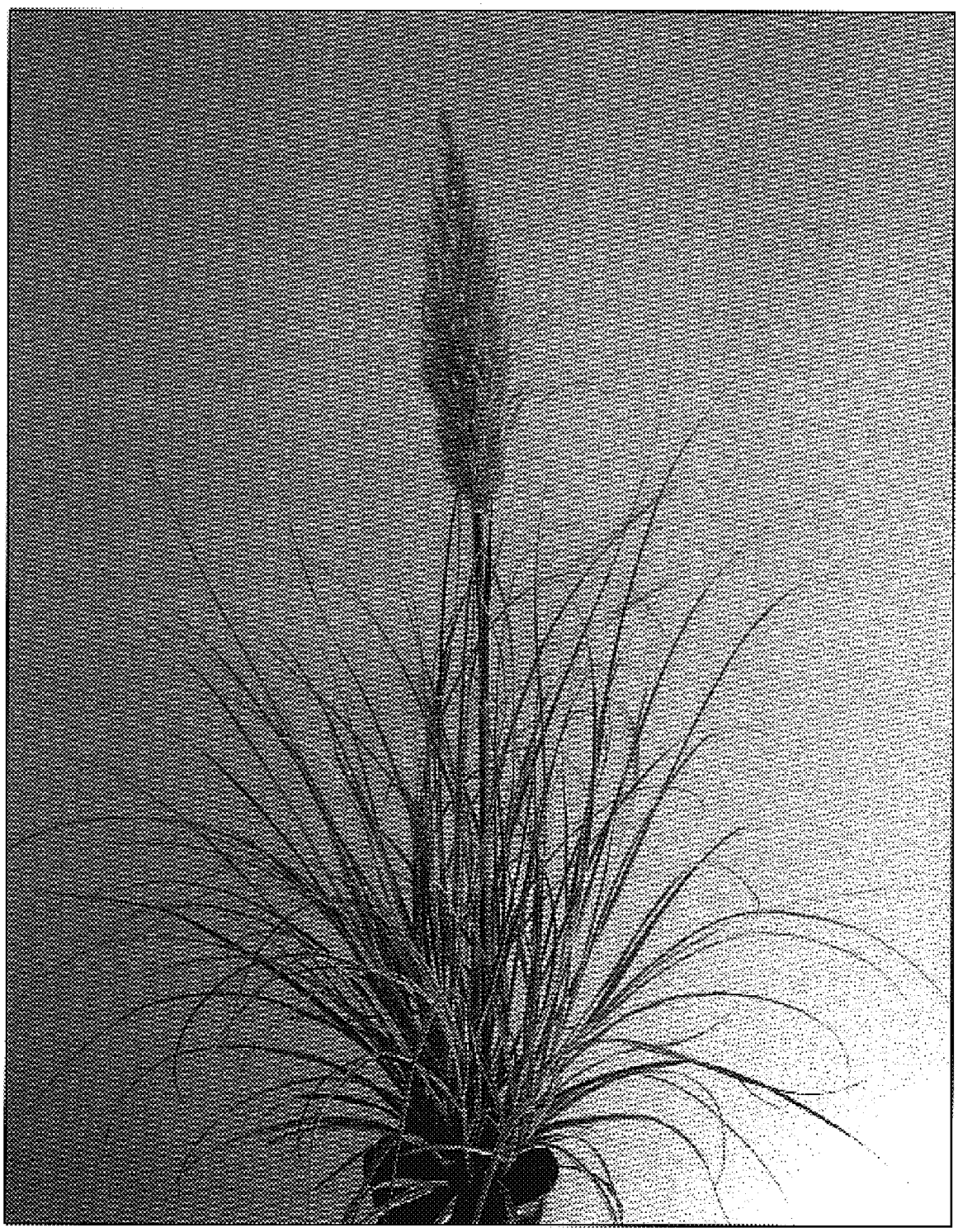
FIG. 1 shows the overall plant habit, including the inflorescence and the foliage.
Figure 2:
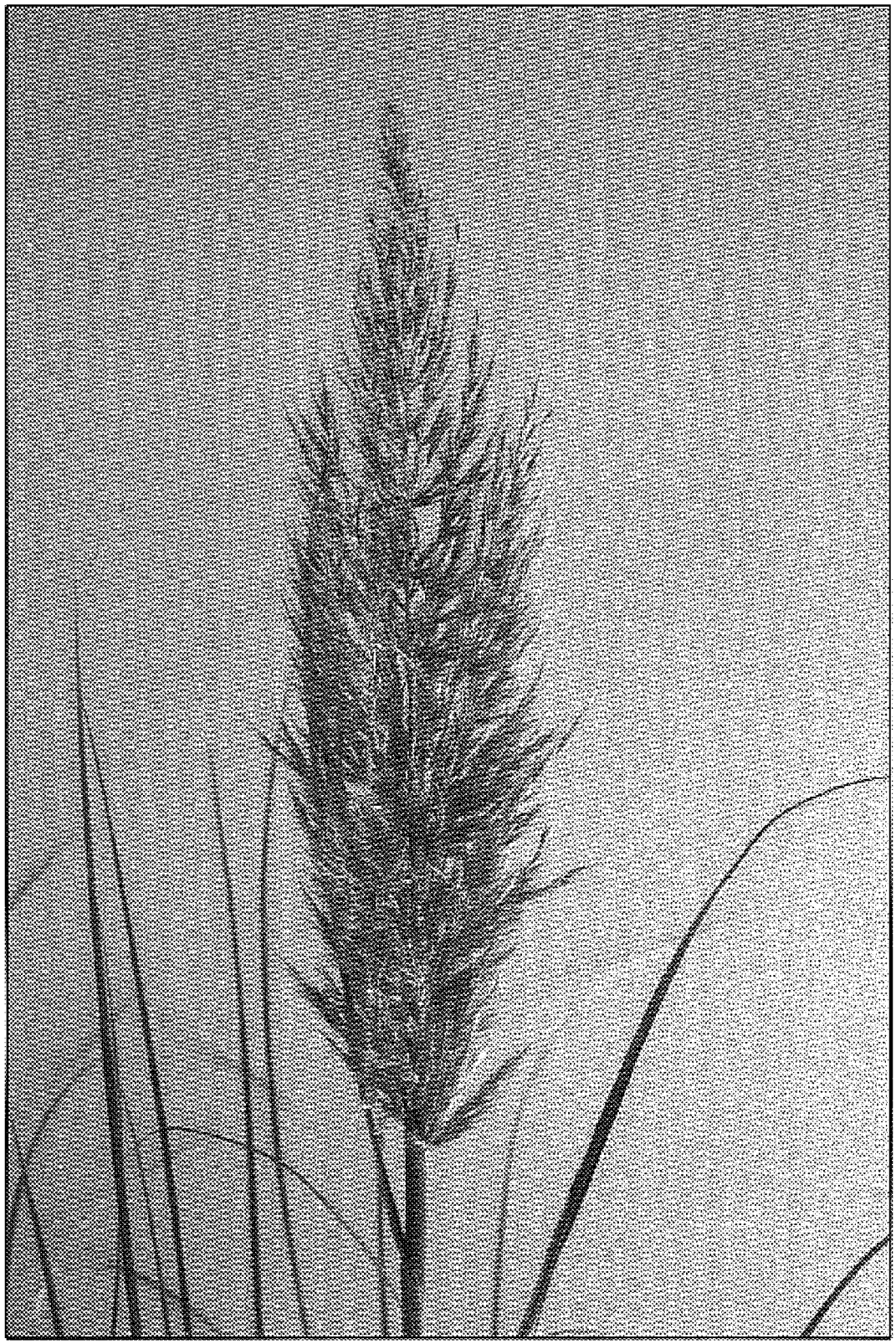
FIG. 2 shows a close-up of the mature inflorescence.
Figure 3:
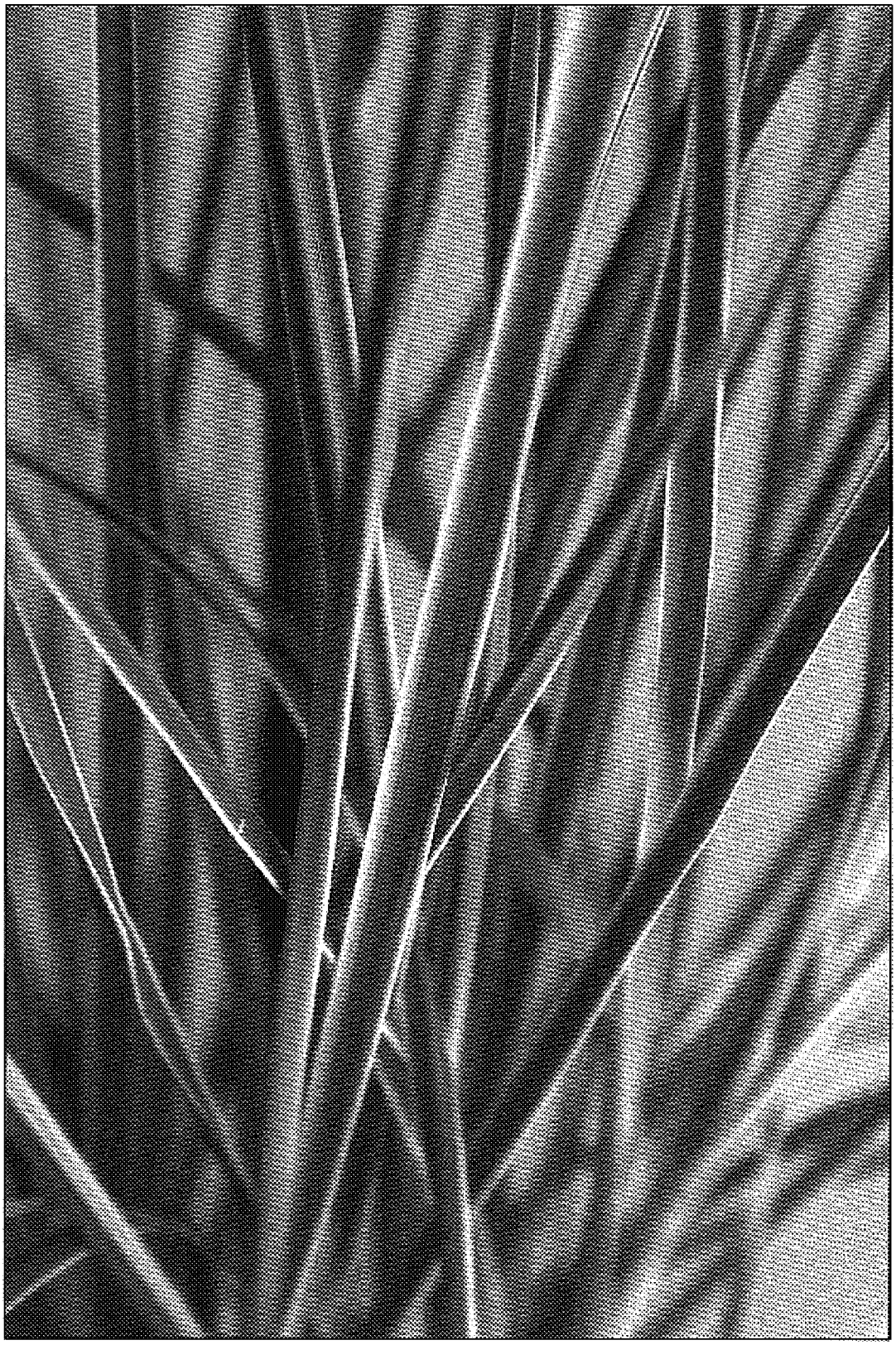
FIG. 3 shows a close-up of the foliage.

The following detailed descriptions set forth the distinctive characteristics of 'Silver Star'. The data which define these characteristics were collected from asexual reproductions carried out in Boskoop, The Netherlands. The plant history was taken on two-year old plants in 19-cm pots in September that were grown outdoors at a temperature range of 4° C. to 32° C. Color readings were taken under natural light outdoors. Color references are primarily to The R.H.S. Colour Chart of The Royal Horticultural Society of London (R.H.S.) (2001).

Classification:
- *Family.*—Poaceae.
- *Botanical name.*—*Cortaderia selloana.*
- *Common name.*—Pampas grass.

Parentage: Whole plant mutation arising from *Cortaderia selloana* 'Pumila' (unpatented).

Growth:
- *Type.*—Herbaceous perennial.
- *Shape.*—Broad inverted triangle with arching leaves and inflorescences on top.
- *Growth habit.*—Broad with arching leaves.
- *Growth rate.*—In the Spring, about 20 cm per month.
- *Height (excluding inflorescences).*—86 cm.
- *Height (including inflorescences).*—105 cm.
- *Width.*—105 cm.
- *Vigor.*—Moderate.
- *Outdoor plant performance.*—Use in container planting or in flower beds.
- *Time to produce a finished flowering plant.*—Average of 9 months.
- *Hardiness.*—Tolerant to at least USDA zone 7.
- *Root description.*—Not fibrous, moderately fleshy.

Leaves:
- *Arrangement.*—Alternate.
- *Type.*—Single.

*Quantity per branch.*—10.

*Attachment.*—Leaf sheaths grow to the base of the shoots; the average width of the sheath is 1.2 cm (when folded open) and RHS 146D (yellow-green) and with a tinge of RHS 179D (greyed-red) at the base.

*Shape.*—Linear.

*Apex.*—Long acuminate.

*Base.*—Cuneate, leaves sheathing.

*Margin.*—Entire but very sharp when rubbed downwards due to very small and sharp teeth with about 18 teeth per centimeter.

*Texture.*—Slightly glossy and smooth; ligules sparsely covered with very RHS 156C to RHS 156D (greyed-white) hairs that are an average of 0.2 cm in length.

*Length.*—59.5 cm.

*Width.*—0.85 cm.

*Venation.*—Parallel.

*Vein color.*—Upper surface: RHS 137C (green) and outer margin is RHS 155A (white) and striped lengthwise with RHS 190B to RHS 190C (greyed-green). Lower surface: RHS 137A to RHS 137B (green) and striped lengthwise RHS 138A to RHS138B and the outer margin is RHS 157A (green-white).

*Color.*—Young leaves: Upper surface: RHS 137C (green) and striped lengthwise with RHS 145B to RHS 145C (yellow-green). Lower surface: RHS 143A (green) and striped lengthwise with RHS 145A (yellow-green). Mature leaves: Upper surface: RHS 137C (green) and outer margin is RHS 155A (white); the leaf blade is striped lengthwise with RHS 190B to RHS 190C (greyed-green). Lower surface: RHS 137A to RHS 137B (green); the leaf blade is striped lengthwise RHS 138A to RHS 138B and the outer margin is RHS 157A (green-white).

*Durability of leaves to stress.*—Very high.

Stems:

*Branching habit.*—Grass-like plant with basal branching; main herbaceous shoots grow from the base; no lateral branching.

*Basal stems.*—Appearance: Rounded, somewhat flattened and slightly glossy. Quantity: Average number of stems is 19. Strength: Very strong. Diameter: 0.5 cm to 0.6 cm; shoots are somewhat flattened. Length: 14.3 cm. Texture: Smooth with no pubescence. Color: RHS 146D (yellow-green) with RHS 179D (greyed-red) tinged at the base.

*Internode length.*—2.5 cm.

Flower buds:

*Quantity per basal stem.*—10,000.

*Shape.*—Lanceolate.

*Length.*—0.4 cm and enclosed by 1 glume and many lemma.

*Diameter.*—0.1 cm.

*Color.*—RHS 145A (yellow-green); glumes and lemma are RHS 196D to RHS 197D (greyed-green).

Inflorescence:

*Arrangement.*—Terminal panicle.

*Aspect.*—Upright to slightly outward.

*Flowering habit.*—Flowers continuously from late August to late October; flowers are persistent.

*Lastingness of flowers on the plant.*—10 days.

*Rate of flower opening.*—After the first flowers open, all flowers will open within two weeks.

*Inflorescence height.*—34.9 cm.

*Inflorescence width.*—11.2 cm.

*Inflorescence shape.*—Feathery.

*Fragrance.*—Absent.

*Diameter.*—0.2 cm.

*Depth (height).*—0.4 cm.

*Quantity per inflorescence.*—Over 10,000.

*Quantity per basal stem.*—10,000.

Flowers:

*Shape.*—Single and grass-like.

*Flower type.*—Single (enclosed by 1 glume and many lemma).

*Color (when opening).*—Both upper and lower surfaces: RHS 196C to RHS 196D (greyed-green).

*Color (fully opened).*—General: Color is greyed-green and does not fade. Both upper and lower surfaces: RHS 196D to RHS 197D (greyed-green).

*Glume.*—Quantity per flower: One. Arrangement: One glume positioned at posterior of the flower. Apex: Narrow acute. Margin: Entire. Shape: Linear. Length: 1.5 cm. Diameter: 0.05 cm. Texture: Smooth and moderately glossy.

*Lemma.*—Quantity per flower: 50. Arrangement: Lemma rotate around flower. Shape: Hair-like. Margin: Entire. Length: 1.5 cm. Diameter: 0.01 cm. Texture: Pubescent.

*Peduncle.*—Length: 66 cm. Diameter: 0.9 cm. Angle: Zero degrees, vertical. Strength: Strong. Color: RHS 138B (green).

*Pedicel.*—Length: 0.2 cm. Diameter: 0.05 cm. Angle: Five degrees. Strength: Strong. Color: RHS 144C (yellow-green).

Reproductive organs:

*Stamens.*—Quantity: 2. Anther shape: Basifixed, feather-like. Anther length: 0.12 cm. Anther color: RHS 145D (yellow-green). Pollen color: RHS N167A to RHS N167B (greyed-orange). Pollen amount: Scarce.

*Pistils.*—None observed.

*Ovary color.*—RHS 146D (yellow-green).

Fruit and seed set: Has not been observed.

Disease and insect resistance: No more susceptible to pests and diseases than other *Cortaderia* varieties.

COMPARISON WITH PARENTAL AND COMMERCIAL CULTIVARS

'Silver Star' differs from the mutation parent 'Pumila' (unpatented) in that 'Silver Star' has green foliage with yellow-green stripes, while 'Pumila' has green foliage with no stripes or markings.

'Silver Star' differs from commercial cultivar 'Splendid Star' (U.S. Plant Pat. No. 16,277) in that 'Silver Star' exhibits no fragrance, while 'Splendid Star' has a slight fragrance. Further 'Splendid Star' has a golden-yellow variegation, whereas 'Silver Star' has a white to green-white variegation.

I claim:

1. A new and distinct variety of *Cortaderia* plant as shown and described herein.

* * * * *